United States Patent [19]

Pruett et al.

[11] Patent Number: 5,218,134
[45] Date of Patent: Jun. 8, 1993

[54] PROCESS FOR ESTERS

[75] Inventors: Roy L. Pruett, Gillette; Edmund J. Mozeleski, Califon, both of N.J.

[73] Assignee: Exxon Chemical Patents Inc., Linden, N.J.

[21] Appl. No.: 950,983

[22] Filed: Sep. 23, 1992

Related U.S. Application Data

[63] Continuation of Ser. No. 75,583, Jul. 20, 1987, abandoned.

[51] Int. Cl.$^5$ ............................................. C11C 3/02
[52] U.S. Cl. .................................................. 560/239
[58] Field of Search ..................................... 560/239

[56] References Cited

U.S. PATENT DOCUMENTS

| | | | |
|---|---|---|---|
| 2,027,378 | 1/1936 | Hale | 560/239 |
| 2,862,013 | 11/1958 | Miller et al. | 260/410.9 |
| 3,188,330 | 6/1965 | Hecker et al. | 260/410.6 |
| 3,957,838 | 5/1976 | Nishino et al. | 560/239 |
| 4,052,424 | 10/1977 | Vanderspurt | 260/410 |

FOREIGN PATENT DOCUMENTS 1177223  1/1970  United Kingdom .

Primary Examiner—Arthur C. Prescott
Attorney, Agent, or Firm—John J. Mahon

[57] ABSTRACT

Esters are prepared directly from 2-substituted alcohols, such as Guerbet alcohols, by dehydrogenating and esterifying the alcohol at 170° C.–240° C. in the presence of a catalyst system comprising (i) platinum on activated carbon, zinc oxide or zinc $C_2$–$C_{20}$ carboxylate and (ii) NaOH, KOH or LiOH. Mixed esters may also be prepared from appropriate mixtures of 2-substituted alcohols.

5 Claims, No Drawings

PROCESS FOR ESTERS

This is a continuation of application Ser. No. 075,583 filed Jul. 20, 1987, now abandoned.

This invention relates to a process for preparing esters directly from alcohols. More particularly, this invention relates to a process for preparing esters by reacting alcohols which are substituted on the 2-carbon position whereby dehydrogenation and esterification occur using certain catalysts.

It is known in the art to prepare Guerbet alcohols, which are branched dimerized or condensed alcohols resulting from the condensation of a primary alcohol or a mixture of primary alcohols. Such alcohols are characterized as containing branching in the 2-carbon position, which is the carbon atom adjacent to the hydroxyl carbon.

Miller et al. in U.S. Pat. No. 2,862,013, issued Nov. 25, 1983, disclose branched-chain higher alcohols formed by condensation of lower alcohols and esters of the higher alcohols. In the preparation of di-tridecyl alcohol, Miller et al. note that di-(tridecyl)tridecanoate can also be formed through oxidation of the starting alcohol to an acid and subsequent esterification with the di-alcohol product. Example 1 of Miller et al. reports the formation of the di-(tridecyl)tridecanoate product, which is a 39-carbon atom ester product. Also, at Column 4, Lines 62-65, the possibility of dimer-dimer esters is mentioned, i.e., by oxidation of the di-tridecyl alcohol to a $C_{26}$ acid with subsequent reaction with a di-tridecyl alcohol. There is no disclosure in Miller et al. of forming esters of Guerbet condensates using the catalysts disclosed in accordance with this invention.

The present invention is based on the discovery that Guerbet alcohols can be used to form esters directly in a dehydrogenation-esterification reaction using certain catalysts and temperatures and at high selectivities and conversions.

In accordance with the present invention there has been discovered a process for preparing an ester of the formula:

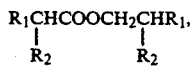

wherein $R_1$ and $R_2$ represent $C_1-C_{20}$ straight chain, branched chain or cyclic alkyl groups, with the proviso that the total of $R_1$ and $R_2$ is at least 4 carbon atoms, which comprises dehydrogenating and esterifying at least two moles of a primary 2-substituted alcohol of the formula:

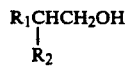

or a mixture of such alcohols at about 170° C.–240° C. in the presence of a two-component catalyst system consisting essentially of (a) at least about 0.0024 wt. % platinum in the form of a dispersion of 1–10 wt. % platinum on a high surface area activated carbon support, 0.4 wt. % zinc oxide or 0.05 wt. % zinc in the form of an alcohol-soluble zinc carboxylate having 2 to 20 carbon atoms and (b) at least about 0.2 wt. % NaOH, KOH or LiOH, said percentages of said catalyst components being based on the amount of alcohol in the reaction mixture.

The process of this invention is therefore a convenient and effective method for providing long chain esters of alcohols such as 2-ethylhexanol and the Guerbet condensate of oxo-isooctanol, which condensate is a $C_{16}$ alcohol. Generally, the preferred alcohols which are subjected to the ester-forming process of this invention are 2-substituted alcohols of the formula:

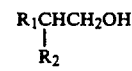

where $R_1$ is a straight or branched chain alkyl having 3 carbon atoms and $R_2$ is a straight or branched alkyl having 2 to 18 carbon atoms. Such alcohols are those which result from the Guerbet condensation of two primary alcohols.

The process of this invention is conducted at a temperature of about 170° C. to 240° C. and preferably at a temperature of about 185° C. to about 200° C. The reaction is effected by adding the catalyst components to the alcohol or alcohols to be reacted and heating the mixture to the desired temperature while removing water and hydrogen which are formed as the reaction proceeds. Reaction times are typically about 2 to 5 hours. Conversions to the ester product have been obtained in the range of about 20 to 75%.

The catalyst system found effective in the present invention comprises two components. The first of these may be (i) platinum dispersed on high surface area activated carbon, (ii) zinc oxide, or (iii) an alcohol-soluble zinc carboxylate salt of a carboxylic acid having 2 to 20 carbon atoms. The preferred catalysts for the first component are platinum on activated carbon wherein 5 wt. % platinum based on the weight of the carbon is present and zinc carboxylates having about 6 to 20 carbon atoms, such as zinc stearate or the zinc salts of neo-acids (acids having a tertiary carbon atom) such as neo-decanoic acid. Zinc carboxylates having less than 6 carbon atoms, while being effective, tend to produce relatively low conversions.

When platinum is used, it is present in an amount of from at least about 0.0024 wt. % platinum up to about 0.1 wt. % platinum, preferably about 0.005 to about 0.008 wt. % platinum being present. The platinum/activated carbon catalyst should have a surface area of at least 500M²/g. and a particle size of less than 200 microns. Preferably it has a surface area of about 1000 to 1200M²/g. (square meters per gram) and a mean particle size of less than 100 microns, such as about 30 microns, with 90% by weight of the activated carbon particles have a particle size less than 70 microns. The amount of platinum dispersed onto the activated carbon may vary from about 1 to 10 wt. % based on the total weight of activated carbon and platinum.

Zinc carboxylate, when present, is used in an amount of from about 0.05 wt. % zinc up to about 5 wt. % zinc, and preferably about 0.1 to 0.3 wt. % zinc is used (present in the form of zinc carboxylate).

For zinc oxide, the amounts may vary from about 0.4 wt. % to about 10 wt. %, with the preferred range being from about 1 to 3 wt. %.

The second component of the catalyst may be sodium hydroxide, potassium hydroxide or lithium hydroxide and this component may be present in amounts from about 0.2 wt. % up to about 20 wt. %, the preferred range being about 4 wt. % to 10 wt. %. NaOH is preferred as the second component catalyst.

The process of this invention is also applicable to the reaction of mixed alcohols to form the corresponding mixed esters. Thus, for example, a branched $C_{16}$ alcohol may be reacted with 2-ethylhexanol and there will be formed a $C_{16}$ ester, a $C_{24}$ ester and a $C_{32}$ ester.

The invention is illustrated by the following examples which are not to be considered as limitative of its scope. The platinum/carbon catalyst used in all examples was 5 wt. % platinum dispersed onto activated carbon powder having a surface area of 1200 $M^2/g$. and a mean particle size of 30 microns with 90% of the powder having a particle size less than 70 microns.

EXAMPLE 1

250 gms. of 2-ethyl-1-hexanol and 16.9 g. 85% KOH were placed in a 4-necked 500 ml. round bottom flask fitted with a magnetic stirrer, thermometer, reflux condenser and Dean-Stark trap. The mixture was heated to reflux (189° C.) for 30 minutes, during which time 6.5 ml. of water distilled into the Dean-Stark trap.

The solution was cooled to ambient temperature and 0.24 g. of 5% platinum on carbon powder was added. The solution was again heated to reflux. After 20 minutes the temperature of the refluxing solution had risen to 190° C. Thereafter the pressure was gradually reduced as needed to maintain a solution temperature of 190° C.

After 5 hours of heating, the mixture was cooled to room temperature and washed twice with aqueous acetic acid and filtered. A gas chromatographic analysis indicated that 50% of the 2-ethyl-1-hexanol had reacted. The principal product was a $C_{16}$ product with a conversion of 44%, which was distilled at reduced pressure. 65.6 g. of liquid distilled at 72° C. and 0.01 mm. Hg. An infrared analysis showed a strong ester band at 1735 $cm^{-1}$ and no band characteristic of alcohol. Thus, the product was 2-ethylhexyl-2-ethylhexanoate.

EXAMPLE 2

The procedure of Example 1 was used. Sodium hydroxide, 9.64 g. was used as the base. The reaction temperature was 195° C. and the time of heating was 4 hours.

After cooling and work-up as described in Example 1, the crude product was analyzed by gas chromatographic techniques. Only 13% of the starting 2-ethylhexanol-1 remained unreacted. The conversion to 2-ethylhexyl-2-ethylhexanoate was 76%, 2.4% was 2-ethylhexanol, and most of the remainder was 2-ethylhexanoic acid.

EXAMPLE 3

The general procedure of Example 1 was used. The amount of NaOH was 3.8 gms., the amount of 5% Pt/C was 0.12 g., the reaction temperature was 181° C.-183° C. and the reaction time was 2 hours, analysis showed 7% conversion to the ester.

EXAMPLE 4

The general procedure of Example 1 was used. The amount of NaOH was 7.6 gms., the amount of 5% Pt/C was 0.36 gms., the reaction temperature was 178° C.-185° C. and the reaction time was 2 hours.

After neutralization and washing, the crude product was analyzed by gas chromatography. The conversion to ester was 31.5%.

EXAMPLE 5

121.3 gms. (0.1 mole) of branched $C_{16}$ alcohol prepared by the Guerbet reaction of oxo isooctanol, 10.0 gms. KOH and 2.0 gm. of zinc oxide were placed in a 4-necked, 500 ml. round-bottom flask fitted with a magnetic stirrer, thermometer, nitrogen bubbler and Dean-Stark trap with reflux condenser attached.

The stirred mixture was heated to 190° C. for 4 hours, while passing nitrogen through the solution to remove any water formed, as well as the hydrogen produced during reaction.

After cooling to ambient temperature, the product was washed twice with aqueous acetic acid. This resulted in a cloudy, slightly viscous, liquid organic product. Analysis showed 22% conversion to ester. This experiment shows that 1) higher chain-length alcohols which are highly branched are satisfactory for this invention and 2) that zinc oxide is a satisfactory catalyst.

EXAMPLE 6

2-Ethylhexanol, 210 g., 10 g. KOH and 0.7 g. zinc acetate dihydrate were placed in a 4-necked, 500 ml. round-bottom flask fitted with a magnetic stirrer, thermometer, and Dean-Stark trap with reflux condenser. The solution was refluxed at 185° C.-187° C. for 2 hours. A sample was taken and analyzed by gas chromatography. Only 2% had been converted to ester.

Zinc stearate (2.0 g.) was added and refluxing continued for 4.5 additional hours, during which time the temperature rose to 195° C. The hazy solution was cooled and washed twice with aqueous acetic acid. The conversion to $C_{16}$ ester was 51%.

This experiment shows that soluble zinc salts are effective catalysts and also are more effective than zinc oxide.

EXAMPLE 7

The procedure of Example 5 was followed with 121.3 g. (0.5 mole) of the branched $C_{16}$ alcohol, 65.1 g. (0.5 mole) of 2-ethylhexanol as reactants with 10 g. KOH and 2.0 g. ZnO as catalyst. The heating at 190° C. was continued for 4 hours. The cooled and washed product analysis showed it to contain 14.0% unreacted 2-ethylhexanol, 33% unreacted $C_{16}$ alcohol, 14% $C_{16}$ ester, 25.6% mixed $C_{24}$ ester and 12.4% $C_{32}$ ester. This experiment shows that the invention is applicable to mixed alcohol reactants.

EXAMPLE 8

The procedure of Example 1 was followed. The amount of NaOH was 0.91 gm., the amount of 5% Pt/C was 0.240 gm. The reaction temperature was 181° C.-186° C., and the reaction time was 3 hours. Analysis of the washed product indicated 28% conversion to ester.

What is claimed is:

1. A process for preparing an ester of the formula:

which comprises dehydrogenating and esterifying at least two moles of a primary 2-substituted alcohol of the formula:

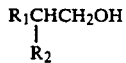

wherein $R_1$ is straight chain or branched chain alkyl having 3 to 20 carbon atoms and $R_2$ is a straight chain or branched chain alkyl having 2 to 18 carbon atoms, or a mixture of such alcohols at about 170° C.–240° C. in the presence of a two-component catalyst system consisting essentially of (a) at least about 0.0024 wt. % platinum in the form of a dispersion of 1–10 wt. % platinum on a high surface area activated carbon support and (b) at least about 0.2 wt. % NaOH, KOH or LiOH, said percentages of said catalyst components being based on the amount of alcohol in the reaction mixture.

2. The process of claim 1 wherein the second component of the catalyst is NaOH present in an amount of about 4 wt. % to about 10 wt. %.

3. The process of claim 1 wherein there is present 0.005 to 0.008 wt. % platinum.

4. The process of claims 1 or 3 wherein the platinum on activated carbon catalyst has a surface area of about 1000 to 1200 $M^2/g$. and a mean particle size of less than 100 microns.

5. The process of claim 1 wherein the temperature is 185° C. to about 200° C.

* * * * *